(12) United States Patent
Kienzle, III

(10) Patent No.: US 7,933,640 B2
(45) Date of Patent: Apr. 26, 2011

(54) INTERCHANGEABLE LOCALIZING DEVICES FOR USE WITH TRACKING SYSTEMS

(75) Inventor: Thomas C. Kienzle, III, Lake Forest, IL (US)

(73) Assignee: General Electric Company, Schenectady, NY (US)

( * ) Notice: Subject to any disclaimer, the term of this patent is extended or adjusted under 35 U.S.C. 154(b) by 1209 days.

(21) Appl. No.: 10/535,092

(22) PCT Filed: Nov. 13, 2003

(86) PCT No.: PCT/US03/36255
§ 371 (c)(1),
(2), (4) Date: May 13, 2005

(87) PCT Pub. No.: WO2004/046754
PCT Pub. Date: Jun. 3, 2004

(65) Prior Publication Data
US 2006/0122495 A1    Jun. 8, 2006

Related U.S. Application Data

(60) Provisional application No. 60/426,314, filed on Nov. 14, 2002.

(51) Int. Cl.
*A61B 5/05* (2006.01)
(52) U.S. Cl. ......... 600/424; 600/407; 600/426; 600/427
(58) Field of Classification Search .................. 600/407, 600/421–424, 439; 128/899; 378/197, 205; 324/207.11–207.13, 207.17; 606/130
See application file for complete search history.

(56) References Cited

U.S. PATENT DOCUMENTS

| 4,583,538 | A | * | 4/1986 | Onik et al. | 606/130 |
|---|---|---|---|---|---|
| 5,197,476 | A | * | 3/1993 | Nowacki et al. | 600/439 |
| 5,230,623 | A | * | 7/1993 | Guthrie et al. | 433/72 |
| 5,309,913 | A | * | 5/1994 | Kormos et al. | 600/429 |
| 5,383,454 | A | * | 1/1995 | Bucholz | 600/429 |

(Continued)

FOREIGN PATENT DOCUMENTS
WO    WO 99/27837    6/1999
(Continued)

OTHER PUBLICATIONS

European Application No. 037819273-2220 office action dated Jul. 30, 2008 (5 pages).

(Continued)

*Primary Examiner* — Unsu Jung
(74) *Attorney, Agent, or Firm* — McAndrews, Held & Malloy, Ltd.; Michael A. Dellapenna

(57) ABSTRACT

A system for tracking the position of an instrument relative to an area of interest includes a first fixator configured to carry first and second localizing devices. A second fixator is configured to carry the first localizing device. A third localizing device communicates with the first localizing device and the second localizing device communicates with the first localizing device such that the position of the second localizing device can be determined relative to the position of the third localizing device. The second localizing device is attachable to the instrument and the first localizing device is attachable to the first fixator such that the first localizing device communicates with the second localizing device on the instrument in order that the position of the second localizing device on the instrument can be determined relative to the third localizing device.

1 Claim, 5 Drawing Sheets

U.S. PATENT DOCUMENTS

| | | | |
|---|---|---|---|
| 5,447,154 A * | 9/1995 | Cinquin et al. | 600/429 |
| 5,622,170 A * | 4/1997 | Schulz | 600/424 |
| 5,638,819 A | 6/1997 | Manwaring et al. | |
| 5,662,111 A * | 9/1997 | Cosman | 600/417 |
| 5,782,765 A * | 7/1998 | Jonkman | 600/424 |
| 5,829,444 A | 11/1998 | Ferre et al. | |
| 5,848,967 A * | 12/1998 | Cosman | 600/426 |
| 5,980,535 A * | 11/1999 | Barnett et al. | 606/130 |
| 5,987,960 A * | 11/1999 | Messner et al. | 73/1.79 |
| 5,999,837 A * | 12/1999 | Messner et al. | 600/407 |
| 6,021,343 A * | 2/2000 | Foley et al. | 600/429 |
| 6,050,724 A * | 4/2000 | Schmitz et al. | 378/205 |
| 6,161,032 A | 12/2000 | Acker | 600/424 |
| 6,235,038 B1 * | 5/2001 | Hunter et al. | 606/130 |
| 6,285,902 B1 | 9/2001 | Kienzle, III et al. | |
| 6,332,089 B1 * | 12/2001 | Acker et al. | 600/424 |
| 6,348,058 B1 * | 2/2002 | Melkent et al. | 606/130 |
| 6,402,762 B2 * | 6/2002 | Hunter et al. | 606/130 |
| 6,478,802 B2 | 11/2002 | Kienzle, III et al. | |
| 6,499,488 B1 * | 12/2002 | Hunter et al. | 128/899 |
| 6,611,141 B1 * | 8/2003 | Schulz et al. | 324/226 |
| 6,636,757 B1 | 10/2003 | Jascob et al. | |
| 6,697,664 B2 | 2/2004 | Kienzle, III et al. | |
| 6,827,723 B2 * | 12/2004 | Carson | 606/130 |
| 6,887,245 B2 * | 5/2005 | Kienzle et al. | 606/80 |
| 6,925,339 B2 * | 8/2005 | Grimm et al. | 700/59 |
| 2002/0032380 A1 * | 3/2002 | Acker et al. | 600/439 |
| 2002/0085681 A1 * | 7/2002 | Jensen | 378/197 |
| 2002/0095081 A1 * | 7/2002 | Vilsmeier | 600/407 |
| 2002/0150215 A1 * | 10/2002 | Barnes et al. | 378/197 |
| 2003/0184285 A1 * | 10/2003 | Anderson et al. | 324/207.17 |
| 2004/0073228 A1 | 4/2004 | Kienzle, III et al. | |
| 2004/0077940 A1 | 4/2004 | Kienzle, III et al. | |

FOREIGN PATENT DOCUMENTS

| | | |
|---|---|---|
| WO | WO 9927837 A2 * | 6/1999 |
| WO | WO 01/01845 | 1/2001 |
| WO | WO 01/30257 | 5/2001 |
| WO | WO 01/54579 | 8/2001 |
| WO | WO 02/061371 | 8/2002 |

OTHER PUBLICATIONS

European Application No. 037819273-2220 office action dated Oct. 28, 2009 (3 pages).

* cited by examiner

INTERCHANGEABLE LOCALIZING DEVICES FOR USE WITH TRACKING SYSTEMS

RELATED APPLICATIONS

This application claims the benefit of, and is a national stage application pursuant to 35 U.S.C. 371 of, PCT International Application No. PCT/US2003/036255, filed on Nov. 13, 2003, which claims priority to provisional application Ser. No. 60/426,314, filed Nov. 14, 2002, and the disclosures of these applications are hereby incorporated in their entirety.

BACKGROUND OF THE INVENTION

The present invention relates to a system and method for tracking localizers. More particularly, certain embodiments of the present invention relate to an electromagnetic tracking system and apparatus used for tracking surgical instruments.

During surgical operations, it is beneficial to be able to track the direction and progress of a surgical instrument, such as a drill bit or screw, into a patient's body in order to ensure that the instrument is directed into the appropriate point in the body. Therefore, surgical tracking systems have been developed that are able to monitor and display movement of a surgical instrument relative to an image of the area of the patient's body where surgery is to take place. The area of the patient's body where surgery is to take place is imaged using an imaging technology such as an X-ray, MRI, CT scan or any other appropriate imaging technology. The scanned images are stored in a computer system and are displayed on a screen during the surgical procedure. The tracking system includes localizing devices on the instrument and patient that communicate with the computer system. The computer system translates the location of the localizing devices onto the image to recreate the relative position of the instrument to the patient.

Surgeons are able to track and predict the position of the instrument within the patient's body by viewing the position of the instrument on the image, and thus accurately align the drill bit or screw into the targeted area of the patient's body. By being able to use surgical tracking surgeons are able to effectively use surgical tools without having to take numerous X-rays during surgery to follow the progress of the surgical instrument. Therefore, operating room staff and patients are exposed to fewer X-rays for each surgical operation. Additionally, surgical tracking presents the potential for increased accuracy and improved surgical outcome.

There are two basic kinds of surgical tracking systems, optical tracking systems and electromagnetic tracking systems. Optical tracking systems use a number of emitters such as light emitting diodes (LEDs) or reflective spheres that are attached to the instruments. A camera system, also known as a digitizer, is used to track the positions of the emitters in space. The camera system is connected to the computer system which analyzes the positions of the emitters as recorded by the camera system to calculate the positions of the emitters, and thus the instruments, on the image.

Electromagnetic tracking systems use electromagnetic transmitters and receivers. The transmitter and receiver are in communication with the computer system. The transmitter generates an electromagnetic field and the receiver receives the field and generates signals to the computer based on the receiver's position in the electromagnetic field. The computer reads the signal from the receiver to calculate the position of the receiver relative to the transmitter. The transmitter is rigidly secured to the patient's body, by bone screws for example, proximate the area of the patient's body where surgery is to take place. A C-arm X-ray machine is connected to the computer system and takes at least one image of the area of the patient's body where surgery is to take place. The C-arm has a receiver that communicates with the transmitter and a calibration device that registers the position of the image relative to the C-arm. Thus, the computer system is able to calculate the position of points of the image relative to the transmitter. A surgical instrument has a receiver that communicates with the computer such that the computer calculates the receiver's position relative to the transmitter. The computer then calculates the position of the receiver relative to the image, and thus displays a representation of the instrument, properly positioned on the image based on these calculations. Alternatively, in some electromagnetic tracking systems, multiple transmitters and/or receivers are positioned relative to the instrument and the patient to track the instrument.

In electromagnetic systems, there are typically restrictions on the distances apart that a transmitter and receiver must be placed in order to yield accurate relative position information. The transmitter and receiver typically must not be too close to one another (e.g., less than a few inches) or too far apart (more than about 18 inches). Additionally, the presence of devices that generate electromagnetic fields, such as an electric drill, can cause interference with the accurate functioning of the localizing system. Likewise, the presence of some metals, such as those used in retractors, operating room tables or fluoroscopic C-arms, can cause interference that produces localizing errors. This interference is especially pronounced when the metal is in close proximity to either the transmitter or receiver, or anywhere in between them. This interference can be minimized by careful placement of the tracking devices relative to one another and to potential sources of interference.

The need to maintain the transmitter and the receiver in close proximity creates difficulties for certain procedures such as total knee surgery. Total knee surgery is an orthopedic procedure in which the articular cartilage of the knee is replaced with prosthetic metal and plastic components. In order to use surgical tracking in the placement of these prosthetic components, the transmitter typically needs to be attached proximate to the patient's knee. The proper positioning of the knee components typically requires that the joint centers of the hip, ankle and knee be collinear, defining the mechanical axis of the knee. One way to identify the joint centers is with x-ray images. However, when the C-arm X-ray machine is used to take images of the hip and ankle, and the transmitter is attached proximate the patient's knee, the distance between adjacent leg joints may be greater than the operating volume of the EM tracking system. Thus, the transmitter and receiver in the C-arm cannot effectively communicate such that the position of the transmitter relative to the image may be calculated. Therefore, images of the hip and ankle cannot be related to the surgical operation of the knee.

Additionally, other kinds of surgery may also involve distances too great to effectively use a conventional electromagnetic tracking system. In the repair of a fracture of the shaft of a long bone, a long rod (intramedullary rod or IM rod) is inserted down the central canal of the bone and rigidly holds the fracture fragments together. A first step in this procedure is the drilling of a hole in one end of the bone (the insertion end) and then inserting a long rod (reduction tool) down the canal to bridge the fracture and align the fragments. A final step in the procedure is the insertion of transverse locking screws into the bone and through holes in the IM rod at the end opposite the insertion end of the bone. During this surgery, the range of positions for a tracking sensor can vary widely. The tracking sensor on the reduction tool may be located at the opposite end from the tool's tip such that, as the tool is first inserted into the bone, the tracking sensor may be as much as 50 cm from the bone. During tracking of a drill to prepare the screw holes for the interlocking screws, the tracking sensor may be as much as 50 cm from the insertion end of the bone. Therefore, the working range for the tracker approaches one meter. Typically, such a distance is too great for a conventional surgical tracking system, especially an electromagnetic tracking system.

Other orthopaedic procedures may create similar difficulties for the surgical tracking system. Therefore, a need exists for an improved method and system for tracking the movement of an instrument relative to joints situated more than a certain distance from the area of surgery.

BRIEF SUMMARY OF THE INVENTION

Certain embodiments of the present invention include a system for tracking the position of an instrument relative to an area of interest. The system includes a first fixator secured to a first point along the area of interest. The first fixator is configured to carry first and second localizing devices. A second fixator is secured to a second point along the area of interest. The second fixator is configured to carry the first localizing device. A third localizing device is positioned proximate a third point along the area of interest. The second point is located proximate the first and third points. The third localizing device communicates with the first localizing device at the second fixator and the second localizing device at the first fixator communicates with the first localizing device at the second fixator such that the position of the second localizing device at the first fixator can be determined relative to the position of the third localizing device proximate the third point. The second localizing device is attachable to the instrument and the first localizing device is attachable to the first fixator such that the first localizing device on the first fixator communicates with the second localizing device on the instrument in order that the position of the second localizing device on the instrument can be determined relative to the first localizing device on the first fixator and to the third localizing device proximate the third point.

Certain embodiments of the present invention include a system for electromagnetically tracking the position of a surgical instrument relative to an image of a patient's body. The system includes a C-arm positioned proximate a first point of the body. The C-arm includes an imaging device and an electromagnetic receiver. A first fixator is joined to the body at a second point proximate an area of interest. The first fixator is configured to carry an electromagnetic receiver and an electromagnetic transmitter. A second fixator is positioned at a third point of the body proximate the first and second points. The second fixator is configured to carry an electromagnetic transmitter. The imaging device takes an image of the body. The transmitter at the second fixator communicates with the receivers at the C-arm and the first fixator such that the position of the receiver at the first fixator can be determined relative to the position of the receiver on the C-arm and the image. The receiver at the first fixator is attachable to the surgical instrument and the transmitter at the second fixator is attachable to the first fixator such that the transmitter communicates with the receiver on the surgical instrument in order that the position of the receiver on the instrument can be determined relative to the transmitter on the first fixator and to the receiver at the C-arm and the image.

Certain embodiments of the present invention include a method for extending the operating range of a tracking system using localizing devices. The method includes connecting a first fixator carrying a first localizing device to a first point proximate an area of interest, connecting a second fixator carrying a second localizing device to a second point proximate the area of interest, and positioning a third localizing device at a third point with the second point being located proximate the first and third points. The method also includes communicating the first and third localizing devices with the second localizing device such that the position of the first localizing device relative to the third localizing device may be calculated. The method further includes removing the first localizing device from the first fixator and attaching the first localizing device to an instrument proximate the area of interest and removing the second localizing device from the second fixator and attaching the second localizing device to the first fixator. The method further includes communicating the first and second localizing devices with each other such that the position of the first localizing device on the instrument relative to the third localizing device may be calculated.

Figure 1:
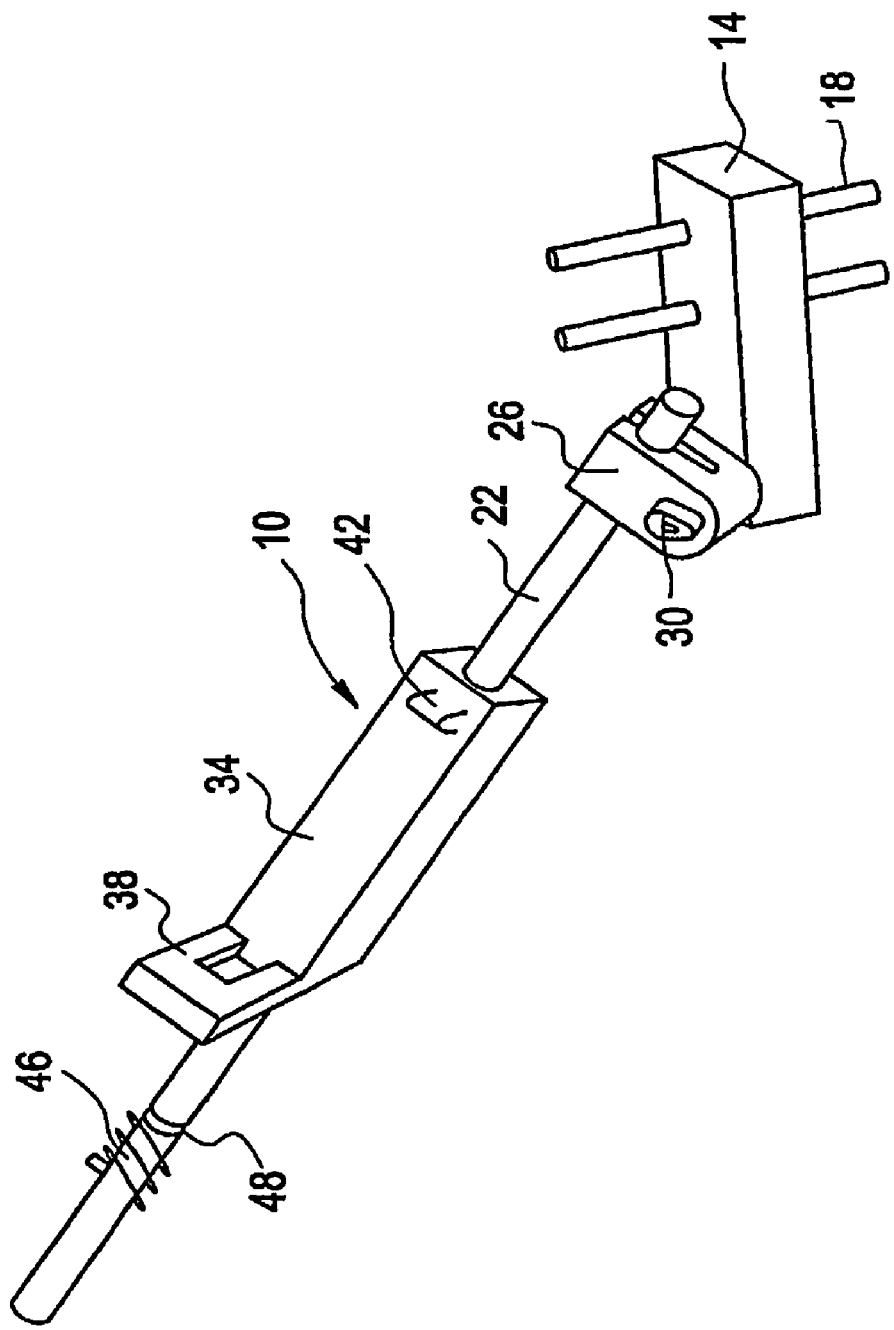
FIG. 1 is an isometric view of a dual fixator formed according to an embodiment of the present invention.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentality shown in the attached drawings.

DETAILED DESCRIPTION OF THE INVENTION

FIG. 1 is an isometric view of a dual fixator 10 formed according to an embodiment of the present invention. The dual fixator 10 includes a substrate shaped attachment block 14 that carries at least one bone screw 18 threaded therethrough. A U-shaped clamp 26 is connected to an end of the attachment block 14 by a screw or bolt 30. The clamp 26 holds a carrier beam 22 that extends away from the attachment block 14. The carrier beam 22 may be rotatable about the screw 30 such that the carrier beam 22 is repositioned at various points relative to the attachment block 14.

The carrier beam 22 includes an L-shaped receiver block 34 connected thereto. The receiver block 34 is configured to receive and carry a localizing device such as an electromagnetic receiver (not shown) between a foot 38 and securing ledge 42. Alternatively, the component may be connected to the receiver block 34 by a different means. The carrier beam 22 also includes a cylindrical transmitter post 46 at an end opposite the attachment block 14. The transmitter post 46 has a spring lock 48 that is configured to engage and retain a localizing device, such as an electromagnetic transmitter (not shown), to the transmitter post 46. Alternatively, the component may be connected to the transmitter post 46 by a different means, such as a threaded connection. The transmitter post 46 and the receiver block 34 are in fixed and known positions relative to one another.

Figure 2:
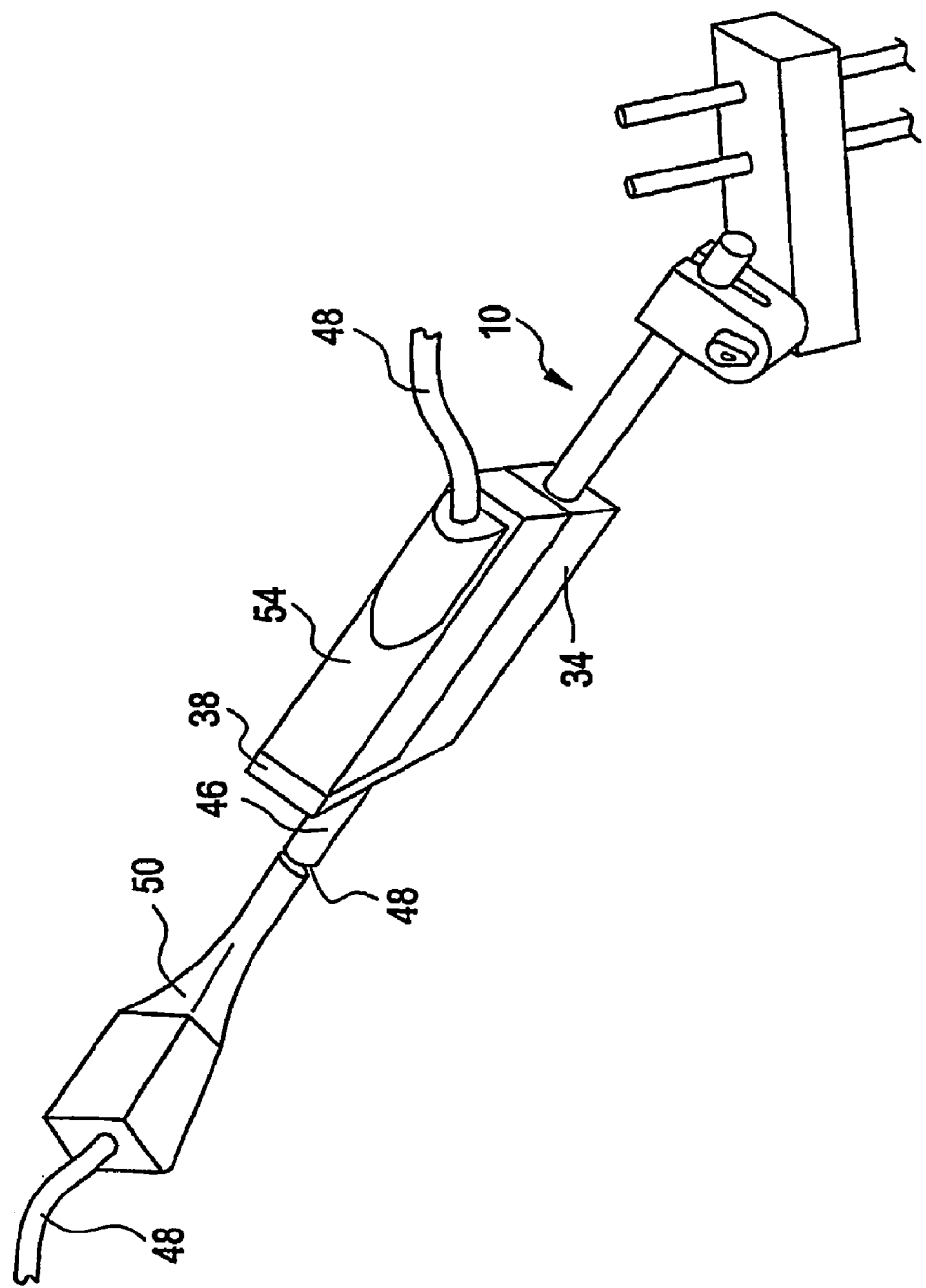
FIG. 2 is an isometric view of the dual fixator of FIG. 1 with both a transmitter and receiver affixed thereto formed according to an embodiment of the present invention.

FIG. 2 is an isometric view of the dual fixator 10 of FIG. 1 with both a transmitter 50 and a receiver 54 affixed thereto. The transmitter 50 is connected to the transmitter post 46 by the spring lock 48, and the receiver 54 is snapably connected to the receiver block 34 along the foot 38 and securing ledge 42 (FIG. 1). The transmitter 50 and receiver 54 are rigidly held in fixed positions relative to one another and, preferably, the relationship between these fixed positions is known prior to use, either by manufacture or calibration. Alternatively, the relationship may be determined at time of use through a calibration procedure in which the receiver 54 and the transmitter 50 are attached to the fixator 10 simultaneously or sequentially, and their relative positions determined. The transmitter 50 and the receiver 54 both have electrical cords 48 connecting them to a computer system (not shown).

Figure 3:
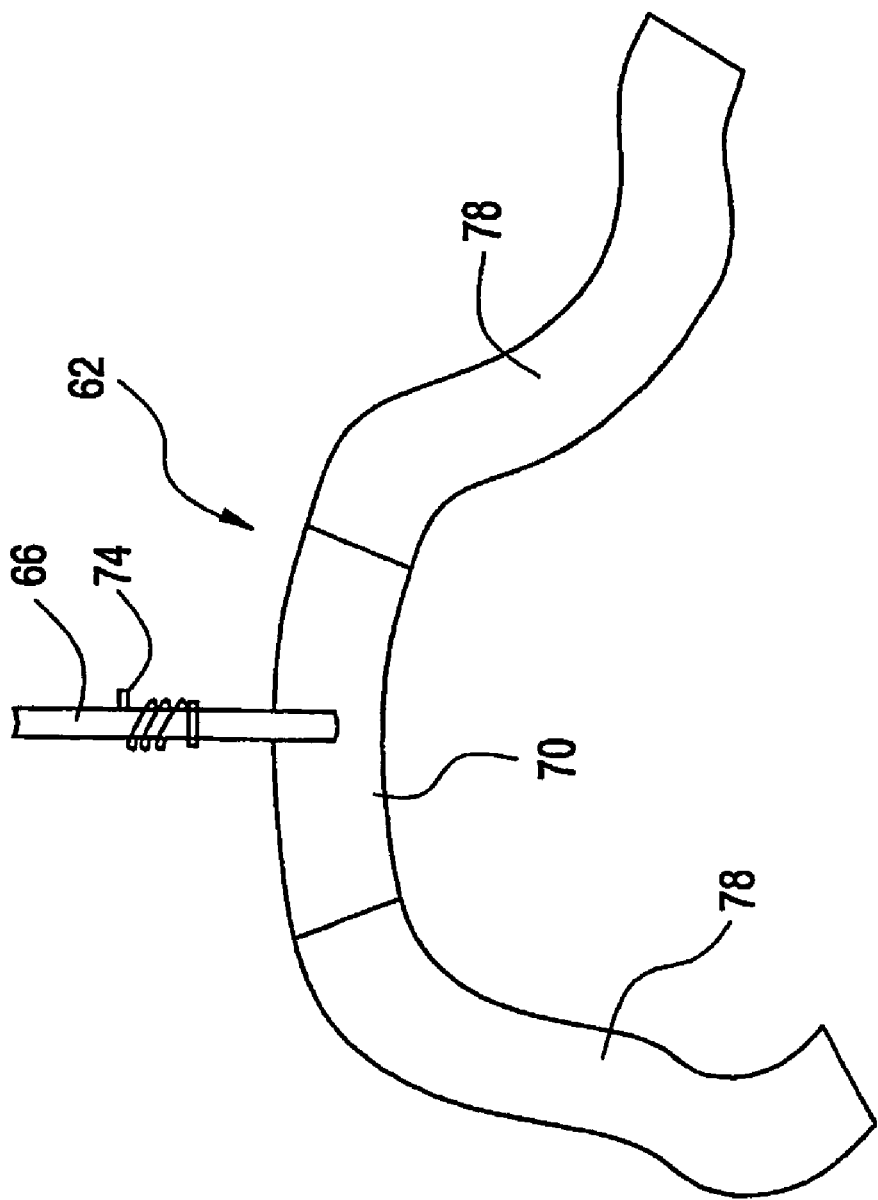
FIG. 3 is an isometric view of a soft tissue fixator formed according to an embodiment of the present invention.

FIG. 3 is an isometric view of a soft tissue fixator 62 formed according to an embodiment of the present invention. The fixator 62 includes a flexible base 70 from which extends a cylindrical transmitter post 66. The transmitter post 66 includes a spring lock 74 in order that a localizing device, such as an electromagnetic transmitter (not shown), may be connected thereto. The fixator 62 includes flexible straps 78 that extend from opposite ends of the flexible base 70. The straps 78 can be wrapped around a patient's limb and connected to each other such that the flexible base 70 is securely connected to the patient's limb. The straps 78 may be VEL-CRO™, however, any other means of attaching the flexible base 70 to the patient may be used such as bone pins, elastic straps, skin adhesives, or skin staples. The transmitter is connected to the transmitter post 66 by the spring lock 74 such that the transmitter is secured to the fixator 62. Alternatively, the transmitter may be attached to an object near the patient, such as the operating table or another structure proximate the patient. Alternatively, any other means, including rigid fixation to the bone, that retains the transmitter relative to the patient may be employed.

Figure 4:
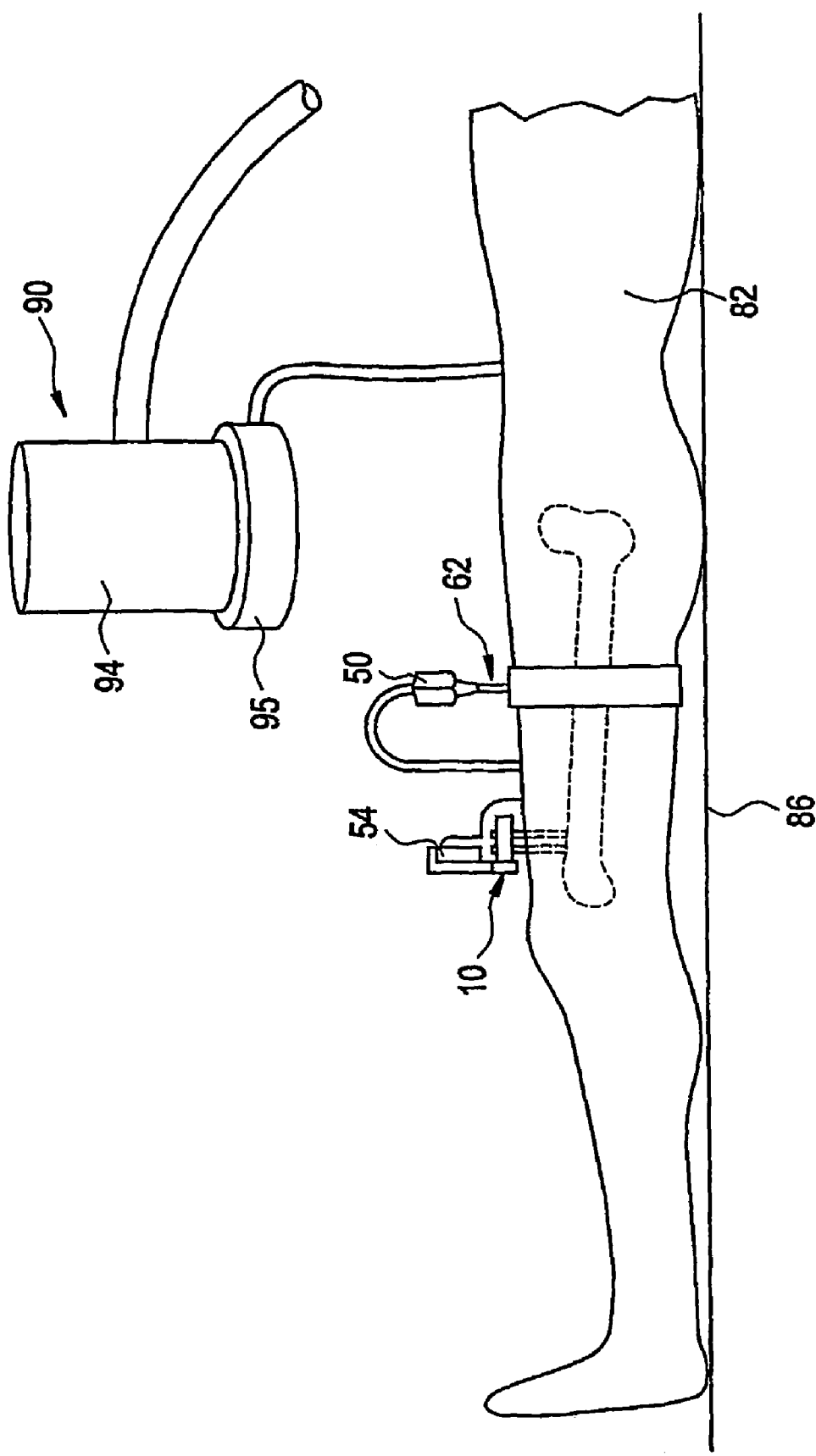
FIG. 4 is an isometric view of the dual fixator of FIG. 1 and the soft tissue fixator of FIG. 3 as used during a surgical operation.

FIG. 4 is an isometric view of the dual fixator 10 of FIG. 1 and the soft tissue fixator 62 of FIG. 3 as used during total knee surgery. A patient 82 lies on an operating table 86. The fixator 10 is affixed to the patient's femur proximal the medial epicondyle of the distal femur and carries the receiver 54. The soft tissue fixator 62 is attached to the patient's thigh and carries the transmitter 50. A movable C-arm 90 is positioned above the patient 82. The C-arm 90 is connected to the computer system (not shown) and includes and imaging device 94 and a calibration target 95 containing calibration points (not shown) and a receiver (not shown). The imaging device 94 takes images of the patient, and computer analysis of the calibration points determine the position of points on the images relative to the receiver on the C-arm 90.

In operation, the transmitter 50 on the fixator 62 sends electromagnetic signals to the receiver 54 on the fixator 10 such that the transmitter 50 and the receiver 54 are in communication. The computer system analyzes the communications to calculate the position of the receiver 54 located at the distal femur relative to the transmitter 50 located at the thigh. The C-arm 90 is positioned and the transmitter 50 on the fixator 62 then sends electromagnetic signals to the receiver on the C-arm 90 such that the transmitter 50 and the receiver are in communication. The computer system analyzes the communications to calculate the position of the receiver relative to the transmitter 50 located at the thigh. The imaging device 94 takes an image of the hip. The computer system then uses the calibration points to determine the position of the points on the image relative to the C-arm 90. By performing mathematical calculations known in the art, the computer system is then able to calculate the position of points on the image relative to the transmitter 50.

The C-arm 90 is withdrawn and the transmitter 50 on the fixator 62 again communicates with the receiver 54 on the fixator 10 to recalculate the position of the receiver 54 relative to the transmitter 50. The first and second calculated relative positions of the transmitter 50 and the receiver 54 are compared. If the comparison indicates that the positions are different, or are different to a degree more than an acceptable or predetermined threshold, than the surgeon may assume that the fixator 62 moved and that the accuracy of the position of the C-arm 90 relative to the transmitter 50 on the fixator 62 is questionable. Movement of the fixator 62 may be attributed to the transmitter 50 being engaged by the surgeon or the C-arm 90, by patient movement, or by an unstable attachment of the fixator 62 to the patient 82. Likewise, motion of the receiver 54 on the fixator 10, while less likely, can also cause a similar error. In case of such an error, the process should be repeated. When the first and second calculated relative positions of the transmitter 50 and the receiver 54 are essentially the same, the surgeon may assume that the fixator 62 did not move relative to the bone. Thus, the surgeon has an accurate record of the position of the transmitter 50 relative to the C-arm 90 and the image. Using mathematical methods known in the art, the computer system can then calculate the position of the receiver 54 relative to the C-arm 90 and the image of the hip.

The foregoing assumes that the C-arm 90 may interfere with the electromagnetic process of measuring the relative position of the receiver 54 to the transmitter 50. Therefore, the C-arm 90 is moved a sufficient distance from the transmitter 50 and receiver 54 so as not to interfere with the electromagnetic signals communicated therebetween. However, if the C-arm 90 is positioned, or is made of a material, such that it does not interfere with the signals, the positions of the C-arm 90 and the receiver 54 relative to the transmitter 50 may be measured simultaneously. Therefore, first and second measurements need not be taken and compared, which saves time and money during the operation.

After the image of the hip is taken, the receiver 54 is removed from the fixator 10 and the transmitter 50 is attached to the fixator 10. The position of the transmitter 50 on the fixator 10 relative to the receiver 54 on the fixator 10 is known or can be determined. By using mathematical methods known in the art, the computer system is then able to calculate the position of the C-arm 90 relative to the transmitter 50 on the fixator 10 at the knee. Thus the surgeon then has an image of the hip and knows where the hip is relative to the position of the transmitter 50 at the knee.

The process may be repeated again at the ankle during total knee surgery. The fixator 10 carries the receiver 54 and is secured to the tibia proximate the knee. The fixator 62 carries the transmitter 50 and is secured to the calf. The C-arm 90 is positioned over the ankle and the position of the transmitter 50 relative to the receiver of the C-arm 90 and the receiver 54 of the fixator 10 is calculated. The C-arm 90 acquires images of the ankle. The position of the transmitter 50 relative to the receiver 54 is again calculated to confirm the accuracy of the first calculated position. The computer system can then calculate the position of the C-arm 90 relative to the receiver 54 to determine the position of the image of the ankle relative to the receiver 54.

Next, the transmitter 50 is connected to the fixator 10 positioned at the femur and the receiver 54 is connected to a second fixator 10 positioned at the tibia. The receiver 54 may be moved from one fixator 10 to the other; alternatively a separate receiver may be used. The position of the receiver 54 is then measured relative to the transmitter 50. The position of the receiver of the C-arm 90 is then measured relative to the transmitter 50. The imaging device 94 of the C-arm 90 then takes an image of the knee, including the proximal tibia and the distal femur. The position of the receiver 54 is then again calculated relative to the transmitter 50 to confirm the first measurement therebetween. The computer system then calculates the positions of the transmitter 50 and the receiver 54 relative to the image. Alternatively, separate images may be taken of the femur and the tibia with the position of a transmitter at each bone being calculated relative to the images.

Once all the images of the hip, ankle, and knee and their relative positions to the transmitter 50 are recorded with the computer system, the images may be used to identify the joint centers. The center of the femoral head may be identified by locating points on the image that lie in the center of the circular femoral head. Alternatively, templates or other graphic or numerical techniques may be used to accurately find the center of the femoral head. Similarly, landmarks visible in the images may be used to enable the surgeon to identify and mark the center of the knee and ankle joints. Alternatively, other non-imaging methods may be used to determine the center of any of the joints. For example, the femur maybe moved through a range of motion at the hip joint, while the system tracks the position of a sensor mounted to the femur, and the joint center of the hip is defined as the center of the sphere segment defined by sensor motion. Similarly, kinematic methods may be used to identify the centers of the knee or ankle, or the surgeon may touch external landmarks with a probe (e.g., medial and lateral malleoulus of the ankle) in order to locate the joint centers.

Once the joint centers are identified and the mechanical axis of the leg defined, cuts in the femur and tibia may be defined and executed to accommodate the total knee components. These are preferably performed with the transmitter 50 placed on the fixator 10 of the bone being resected and the receiver 54 connected to the cutting block or other instrument being employed. The receiver 54 may be moved from the fixator 10 to the instrument; alternatively a separate receiver may be used. Thus, with the transmitter 50 and receiver 54 in electromagnetic communication, the computer system is able to track the movements of the instrument relative to the transmitter 50. Because the position of the transmitter 50 has been calculated relative to the images of the hip, ankle and knee, the position of the instrument may also be calculated relative to the images of the hip, ankle, and knee. The computer system then recreates the position of the instrument on the images such that the surgeon may visually track the instrument relative to any points on the images of the hip, ankle, and knee.

In an alternative embodiment, kinematic analysis of the knee can be performed with a transmitter 50 on the femur and a receiver 54 on the tibia, or vice versa. The surgeon places the knee through a range of motion and applies stresses to the joint while the tracking device records accurate position data for both the femur and tibia. This data can be analyzed by the computer system in order to better define depths of cuts, sizing of components, need for soft tissue adjustments, and the optimum positioning and orientation of the components relative to the images.

Figure 5:
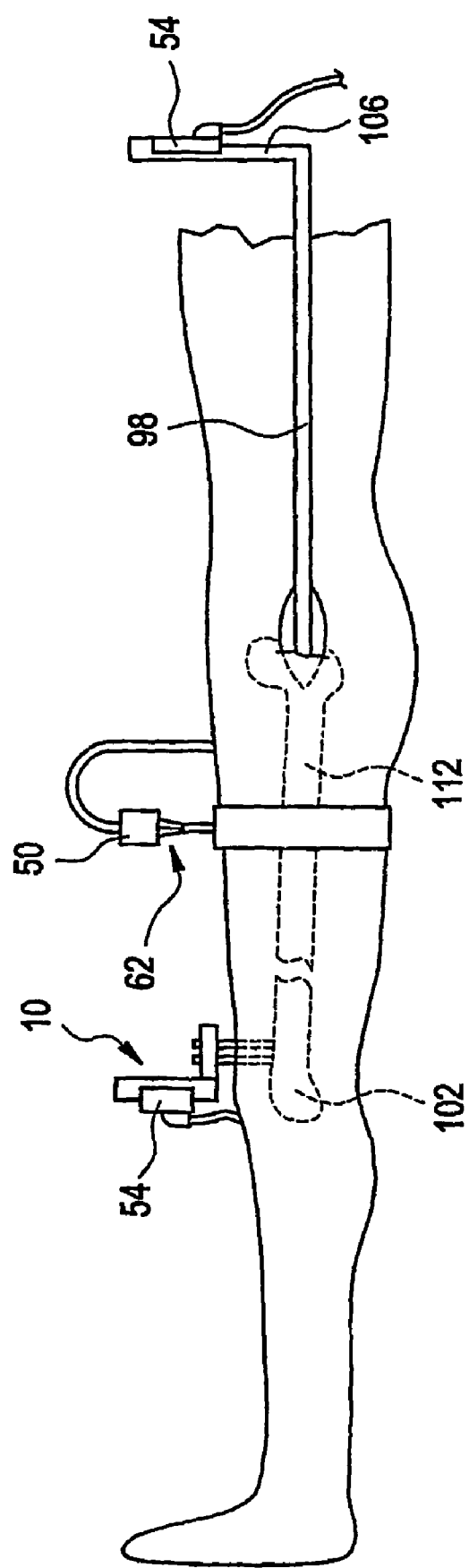
FIG. 5 is an isometric view of the dual fixator of FIG. 1 and the soft tissue fixator of FIG. 3 as used in connection with the reduction and fixation of a long bone with a soft fracture.

FIG. 5 illustrates an alternative use for the system shown in FIG. 4. The procedure shown in FIG. 5 is the reduction and fixation of a long bone with a shaft fracture. Prior to placing an intramedullary rod down a fractured femur 112, a long reduction tool 98 is inserted down the shaft of the femur 112 for the purpose of bridging the fracture site and aligning the fragments. The reduction tool 98 has a handle 106 that carries a tracking receiver 54. As the tip of the reduction tool 98 is first inserted into a first end of the femur 112, the distance between a distal bone fragment 102 and the handle 106 of the reduction tool 98 can be over twice the length of the femur.

In order to track the reduction tool 98 relative to the distal bone fragment 102, the fixator 10 is attached to the distal fragment 102 as shown in FIG. 5. The transmitter 50 is connected to the fixator 10 and images are taken of the distal bone fragment 102 such that the position of the transmitter 50 relative to the image of the fragment 102 may be calculated. The transmitter 50 is then removed from the fixator 10 and replaced by the receiver 54. The transmitter 50 is then connected to the fixator 62 which is attached to the patient's thigh proximate the insertion site of the reduction tool 98. Alternatively, the transmitter 50 may be rigidly attached to the proximal bone fragment or any structure. A second receiver 54 is then attached to the reduction tool 98 at the handle 106 and the reduction tool 98 is then inserted into the femur 112. Because the positions of the transmitter 50 on the fixator 10 and the receiver 54 on the fixator 10 are known relative to one another or may be determined, the computer system is able to calculate the position of the receiver 54 on the fixator 10 relative to the image. The position of the receiver 54 at the distal bone fragment 102 and the position of the receiver 54 on the reduction tool 98 are then simultaneously measured relative to the transmitter 50 at the fixator 62.

The computer system then calculates the position of the reduction tool 98 relative to the image of the bone fragment 102. This information is recorded and shown on the image such that the surgeon may track the movement of the reduction tool 98. Alternatively, additional receivers may be rigidly attached to other fragments and images may be taken of the fragments in order that the movement of the reduction tool 98 may be tracked relative to the other fragments.

While the foregoing describes an interchangeable localizing device system for accommodating surgical tracking over relatively large distances in total knee surgery and shaft fracture repair surgery, it should be understood that this system applies equally well to any procedure which involves similar distances. Additionally, if still greater distances than these may be involved, the distances may be accommodated by additional transmitters and/or receivers spaced apart over the additional distance and in communication with one another. Even without additional sensors, the longer distances may be accommodated by moving a transmitter and receiver pair sequentially among a series of rigidly placed dual fixators. Also, the method disclosed may use transmitters where receivers are used and receivers where transmitters are used. Further, while the foregoing describes the use of an electromagnetic transmitter and receiver, it should be noted that any tracking system may benefit from these techniques and apparatus. For example, emitters used in optical tracking systems may be interchangeably positioned along a surgical area of interest as described above in regard to the transmitters and receivers.

Alternatively, two instruments separated by large distance during surgery may be tracked relative to each other and an image. For example, one instrument may carry a first receiver and the other instrument may carry a second receiver. A transmitter may be positioned between the instruments with its position known (or its position may be determined) relative to an image of the surgical area of interest. The transmitter communicates with the receivers on the instruments and the computer system in order that a surgeon may track the positions of the instruments relative to each other and to the image. Again, localizers besides electromagnetic transmitters and receivers may be used in the alternative.

Alternatively, two instruments separated by a large distance during surgery may be tracked relative to each other and an image by use of at least two fixators. A first fixator is connected at a first point proximate an area of interest and carrying a receiver and a second fixator is connected at a second point proximate the first point and carrying a transmitter. A first instrument carries a receiver which communicates with the transmitter on the second fixator such that the position of the receiver on the first instrument can be determined relative to the transmitter. The transmitter communicates with the receiver on the first fixator in order that the position of the receiver on the first instrument can be determined relative to the position of the receiver at the first fixator. A second instrument carries a transmitter which communicates with the receiver on the first fixator in order that the position of the transmitter on the second instrument can be determined relative to the receiver on the first fixator and to the position of the receiver on the first instrument.

Alternatively, in the example of the two instruments and two fixators, the first fixator connected at the first point may be configured to carry a transmitter and a first receiver with the positions of the transmitter and the first receiver on the first fixator being fixed and known relative to one another. The second fixator may be configured to carry the transmitter and the first instrument, may carry a second receiver that communicates with the transmitter on the second fixator in order that the position of the second receiver can be determined relative to the transmitter. The transmitter in turn communicates with the first receiver on the first fixator such that the position of the second receiver on the first instrument can be determined relative to the position of the first receiver on the first fixator. The second instrument may be configured to carry a third receiver that communicates with the transmitter on the first fixator in order that the position of the third receiver on the second instrument can be determined relative to the transmitter on the first fixator and thus to the position of the second receiver on the first instrument.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method of determining the position of an image of a first area of interest relative to a second area of interest comprising the steps of:

connecting a first fixator carrying a first localizing device to a first point proximate said first area of interest;

connecting a second fixator carrying a second localizing device to a second point proximate said second area of interest;

providing an imaging device configured to acquire an image of an area of interest and carrying a third localizing device;

determining a first position of said third localizing device relative to said second localizing device;

determining a first position of said first localizing device relative to said second localizing device;

acquiring an image of said first area of interest with said imaging device;

determining a second position of said third localizing device relative to said second localizing device;

determining a second position of said first localizing device relative to said second localizing device;

calculating the difference between said first and second positions of said first localizing device relative to said second localizing device and the difference between said first and second positions of said third localizing device relative to said second localizing device;

calculating the position of said third localizing device relative to said first localizing device if said difference is less than a predetermined threshold; and indicating an error if said difference is greater than said predetermined threshold.

* * * * *